United States Patent [19]

Drake

[11] Patent Number: 4,940,829
[45] Date of Patent: Jul. 10, 1990

[54] HYDRODEMETHYLATION OF NEOHEXANE

[75] Inventor: Charles A. Drake, Nowata, Okla.

[73] Assignee: Phillips Petroleum Company, Bartlesville, Okla.

[21] Appl. No.: 260,840

[22] Filed: Oct. 18, 1988

[51] Int. Cl.$^5$ ................................................ C07C 4/10
[52] U.S. Cl. ..................................... 585/752; 585/708
[58] Field of Search ................................. 585/708, 752

[56] References Cited

U.S. PATENT DOCUMENTS 2,422,670  6/1947  Haensel ................................. 585/752
2,422,671  6/1947  Haensel ................................. 585/752
2,422,674  6/1947  Haensel ................................. 585/752
2,422,675  6/1947  Haensel ................................. 585/752

FOREIGN PATENT DOCUMENTS 122162  9/1946  Australia ............................. 585/752

Primary Examiner—Asok Pal
Attorney, Agent, or Firm—K. K. Brandes

[57] ABSTRACT

Neopentane is prepared by reaction of neohexane with free hydrogen, in the presence of the supported palladium catalyst, which preferably additionally contains nickel and/or cobalt.

18 Claims, No Drawings

HYDRODEMETHYLATION OF NEOHEXANE

BACKGROUND OF THE INVENTION

In one aspect, this invention relates to a catalytic hydrodemethylation process. In another aspect, this invention relates to the conversion of neohexane (2,2-dimethylbutane) to neopentane (2,2-dimethylpropane).

SUMMARY OF THE INVENTION

It is an object of this invention to convert neohexane to neopentane.

In accordance with this invention, a process for preparing neopentane comprises the step of contacting a feed comprising neohexane with free hydrogen and a catalyst comprising an inorganic refractory support material (preferably alumina) and palladium metal, under such reaction conditions as to convert at least a portion of neohexane to neopentane.

In a particularly preferred embodiment, the catalyst composition comprises palladium metal and at least one metal selected from the group consisting of cobalt and nickel.

DETAILED DESCRIPTION OF THE INVENTION

Any feed comprising neohexane (boiling point at atmospheric conditions: about 121° F.; melting point: about −48° F.) is suitable as feed in the process of this invention. Preferably, the feed consists essentially of neohexane. The feed can be substantially pure neohexane (presently preferred) or a solution of neohexane in a suitable solvent which is stable and nonreactive under the reaction conditions of this invention (such as normal paraffins, unsubstituted cycloparaffins, benzene and the like).

Free hydrogen can be supplied as substantially pure hydrogen gas (preferred) or as a free hydrogen containing gas mixture, such as a mixture of $H_2$ and $N_2$, or a mixture of $H_2$ and He or Ar and the like, or a mixture of $H_2$ and any other gas which does not react under the reaction conditions of this invention.

The catalyst composition which is employed in the process of this invention can be prepared by any suitable means. Generally, a suitable inorganic support material is impregnated with a solution (preferably aqueous) of a suitable palladium compound, and the thus-impregnated material is dried, calcined, and then reduced. Suitable support materials include alumina, silica, titania, zirconia, magnesia, silica-alumina, alumino silicates (clays or zeolites), aluminum phosphate, and the like, and mixtures thereof. The preferred support material is alumina. Non-limiting examples of suitable palladium compounds are palladium(II) chloride, palladium(IV) chloride, palladium(II) nitrate, $Pd(NH_3)_4(NO_3)_2$, $H_2PdCl_6$, Pd(II) carboxylates, Pd(IV) carboxylates, and the like, and mixtures of the above; preferably $Pd(NH_3)_4(NO_3)_2$.

The impregnation of the support material with the dissolved palladium compound can be carried out in any suitable manner, e.g., by soaking of the support material with the solution (preferably aqueous) of the palladium compound or by spraying the solution onto the support material. The concentration of the palladium compound in the impregnating solution and the weight ratio of solution to support material are such as to attain the desired palladium content in the finished catalyst composition. The thus-impregnated material is substantially dried by any suitable means (preferably in air, at about 8°–150° C., for about 0.5–10 hours) and thereafter calcined (preferably in air) so as to at least partially decompose the palladium compound (preferably at about 200° to about 500° C., for about 0.5 to about 8 hours). Finally, the calcined material is reduced in any suitable manner, preferably by heating in a reducing gas, such as hydrogen (preferred), carbon monoxide, methane, and the like, or a mixture of the above gases.

The reduction step will substantially convert the palladium compounds which are present after calcining, to palladium metal. Preferred reducing conditions comprise a temperature of about 100° to about 450° C., and a reducing time of about 10 minutes to about 5 hours. It is within the scope of this invention to carry out the reducing step at the beginning of the hydrodemethylation process of this invention, i.e., to pass a mixture of hydrogen gas and neohexane over the unreduced palladium catalyst under such conditions as to reduce the palladium to its metallic state.

Preferably, the palladium content (essentially as palladium metal) is in the range of from about 0.2 to about 20 weight-% Pd, more preferably about 0.5–10 weight-% Pd; and the BET surface area (determined by the method of Brunauer, Emmett and Teller, employing $N_2$) is in the range of from about 20 to about 700 $m^2/g$, more preferably about 100–300 $m^2/g$. The palladium catalyst can be ground, sieved and shaped (e.g., to cylindrical extrudates, pellets, tablets, and the like).

In a preferred embodiment, the palladium catalyst composition additionally comprises nickel or cobalt or both nickel and cobalt. In this preferred embodiment, the nickel and/or cobalt catalyst compounds can be incorporated into the palladium catalyst composition in any suitable manner. For example, the impregnating solution containing the palladium compound can additionally contain at least one Ni compound or at least one Co compound or a mixture of Ni and Co compounds (followed by drying, calcining and reducing, as described above). In lieu of the above-described simultaneous impregnation, the Ni and/or Co compounds can also be incorporated by sequential impregnation, such as by impregnation of Pd-impregnated support material (preferably after the drying step), or by impregnation of the starting support material with at least one nickel compound and/or at least one cobalt compound, followed by drying and impregnating with at least one palladium compound. The thus sequentially impregnated material can then be dried, calcined and reduced, as described above.

Suitable nickel compounds include nickel(II) nitrate, nickel(II) sulfate, nickel(II) chloride, nickel(II) bicarbonate, nickel(II) carboxylates (such as formate, acetate, oxalate etc), amino complexes of Ni, and the like, preferably nickel nitrate. Suitable cobalt compounds include cobalt(II) nitrate, cobalt(II) chloride, cobalt(II) bicarbonate, cobalt(II) carboxylates (such as formate, acetate or oxalate etc., cobalt(II) acetylacetonate, amino complexes of cobalt, and the like, and mixtures of the above; preferably cobalt nitrate. The concentration of the Ni and/or Co compounds in the impregnation solution and the ratio of the impregnating solution to the support material are such as to provide the desired Ni and/or Co content in the catalyst.

In a preferred embodiment, the catalyst composition comprises about 0.2 to about 20 weight-% Pd and about 2 to about 30 weight-% Ni, or about 2 to about 30 weight-% Co, or about 2 to about 30 weight-% Ni+Co. More preferably, the palladium catalyst composition contains about 0.5–10 weight-% Pd and about 4–20 weight-% Ni or about 4–20 weight-% Co. The BET surface area of the Pd/Ni or Pd/Co catalyst is about the same as has been described above for the palladium catalyst.

Any suitable contacting conditions for at least partially converting neohexane to neopentane can be employed in the process of this invention. The process can be carried out as a batch process or as a continuous process. The neohexane feed and the free hydrogen containing gas can be introduced into any suitable reaction vessel (which contains the catalyst composition), in any suitable manner. The catalyst composition can be present in a fixed catalyst bed (preferred), or can be dispersed in the reaction mixture (which can be agitated).

Suitable reaction conditions comprise a reaction temperature of about 50° to about 400° C. (preferably about 100°–350° C.); a hydrogen pressure of about 5 to about 1,000 psia (preferably about 14–200 psia), a molar ratio of $H_2$ to neohexane in the range of from about 0.5:1 to about 20:1 (preferably about 0.7:1 to about 5:1), and a reaction time (i.e., time of contact between neohexane, hydrogen and catalyst composition) in the range of from about 1 second to about 10 hours (preferably about 1–60 minutes). Suitable flow rates of neohexane feed and hydrogen gas, amount of catalyst and geometric dimensions of the reactor depend on the desired scale of the operation, the desired reaction rate, and the employed reaction conditions. Generally, a liquid hourly space velocity (i.e., cc liquid neohexane per cc catalyst composition per hour) of about 0.1 to about 20 cc/cc/hour is used.

The desired product (neopentane) can be recovered by separating it from by-products (e.g., methane, isobutane) and from unconverted feed components by any suitable separation means, such as flashing, distillation, membrane separation, absorption, and the like, as can easily be determined by one having ordinary skill and knowledge in chemical engineering.

The desired product, neopentane, has a boiling point under atmospheric pressure conditions of about 49° F. and a melting (solidification) point of about 2° F., and is useful as a refrigerant (mainly because of its low boiling point and low solidification point) or as a heat exchange medium.

The following examples are presented to further illustrate the invention, and are not to be considered as unduly limiting the scope of this invention.

EXAMPLE I

This example illustrates the preparation of catalysts employed in the hydromethylation of neohexane to neopentane.

Catalyst A was prepared by mixing 50 grams of alumina extrudates (provided by Norton Company, Worcester, MA, under the product designation SA-6175; surface area: about 240 $m^2$/g) with a solution of 50 grams $Ni(NO_3)_2$ in 50 cc water. The formed paste was dried by heating in a rotary evaporator, and calcined in air at about 350° C. for about 3 hours. Catalyst A contained about 20 weight-% Ni.

Catalyst B was prepared by mixing 50 g of SA-6175 alumina with a solution of 2 grams $Pd(NH_3)_4(NO_3)_2$ in 50 cc water. The paste was dried, as described above, and calcined in air at about 350° C. for about 2 hours. Catalsyt B contained 1.7 weight-% Pd.

Catalyst C was prepared by mixing 50 g of SA-6175 alumina with a solution of 25 g $Ni(NO_3)_2$ and 2 g $Pd(NH_3)_4(NO_3)_2$ in 50 cc water, followed by drying and calcining, as described for Catalyst B. Catalyst C contained 1.7 weight-% Pd and 10.1 weight-% Ni.

Catalyst D was prepared in accordance with the preparation procedure for Catalyst C except that the aqueous impregnating solution contained 4 g $Pd(NH_3)_4(NO_3)_2$ (in lieu of 2 g). Catalyst D contained 3.4 weight-% Pd and 10.1 weight-% Ni.

Catalyst E was prepared in accordance with the preparation procedure for Catalyst C except that 25 g $Co(NO_3)_2$ was used (in lieu of $Ni(NO_3)_2$). Catalyst E contained 1.7 weight-% Pd and 10 weight-% Co.

EXAMPLE II

This example illustrates the conversion of neohexane (2,2-dimethylbutane) to neopentane (2,2-dimethylpropane). A stainless steel reactor (diameter: about 0.5 inch; length: about 20 inches) was filled with 30–50 g of one of the catalyst compositions described in Example I, and heated to about 220° C. Liquid neohexane was introduced at a rate of 0.5 cc/minute, and hydrogen gas was introduced at a rate of about 60 cc/minute. The reactor effluent, which contained unconverted neohexane, unconverted hydrogen, neopentane, isobutane and methane, was analyzed by means of a gas chromatograph. Test results are summarized in Table I.

TABLE I

| Run | Catalyst | Temp. (°C.) | Hours on Stream | % Conversion of Neohexane | % Selectivity[1] to Neopentane |
|---|---|---|---|---|---|
| 1 | A (30 g) | 210 | 1 | 0 | — |
|   |   | 231 | 1.5 | ~2 | ~100 |
|   |   | 224 | 2 | ~1 | ~100 |
| 2 | B (50 g) | 211 | 1 | 10 | 39 |
|   |   | 225 | 1.5 | 16 | 32 |
|   |   | 234 | 2 | 21 | 30 |
|   |   | 233 | 2.5 | 20 | 29 |
|   |   | 232 | 3 | 39 | 28 |
|   |   | 233 | 3.5 | 16 | 30 |
|   |   | 232 | 4 | 38 | 36 |
|   |   |   | Average: | 23 | 32 |
| 3 | C (34 g) | 218 | 1 | 30 | 90 |
|   |   | 216 | 1.5 | 28 | 88 |
|   |   | 220 | 2 | 30 | 88 |
|   |   | 220 | 2.5 | 29 | 88 |
|   |   | 211 | 3 | 20 | 84 |
|   |   | 217 | 3.5 | 27 | 85 |
|   |   | 222 | 4 | 14 | 86 |
|   |   |   | Average: | 25 | 87 |
| 4 | D (37 g) | 218 | 1 | 51 | 60 |
|   |   | 219 | 1.5 | 50 | 61 |
|   |   | 219 | 2 | 51 | 56 |
|   |   | 210 | 2.5 | 50 | 62 |
|   |   | 209 | 3 | 43 | 68 |
|   |   | 211 | 3.5 | (10)[2] | (48)[2] |
|   |   | 210 | 4 | 58 | 60 |
|   |   | 212 | 4.5 | 56 | 59 |
|   |   | 212 | 5 | 57 | 58 |
|   |   |   | Average: | 52 | 61 |
| 5 | E (32 g) | 218 | 1 | 55 | 61 |
|   |   | 220 | 1.5 | 55 | 57 |
|   |   | 221 | 2 | 54 | 58 |
|   |   | 220 | 2.5 | 55 | 59 |
|   |   | 220 | 3 | 53 | 59 |
|   |   | 221 | 3.5 | 53 | 59 |
|   |   | 220 | 4 | 59 | 60 |
|   |   | 220 | 4.5 | 51 | 60 |
|   |   | 220 | 5 | 52 | 61 |
|   |   | 222 | 5.5 | 55 | 61 |

TABLE I-continued

| Run | Catalyst | Temp. (°C.) | Hours on Stream | % Conversion of Neohexane | % Selectivity[1] to Neopentane |
|---|---|---|---|---|---|
| | | 220 | 6 | 56 | 62 |
| | | | Average: | 54 | 60 |

[1]Neopentane Yield ÷ Neohexane Conversion × 100
[2]Erroneous result; not included in average Test results in Table I show that the nickel catalyst (Catalyst A) was substantially inactive for catalyzing the hydrodemethylation of neohexane to neopentane, whereas palladium-promoted catalysts B–E were quite effective in catalyzing the above reaction. The catalyst which provided highest neopentane yields (conversion x selectivity) were those containing both Pd and Ni or Co (Catalysts C, D and E).

Reasonable variations, modifications and adaptations for various usages and conditions can be made within the scope of the disclosure and the appended claims, without departing from the scope of this invention.

That which is claimed is:

1. A process for preparing neopentane comprising the step of contacting a feed comprising neohexane with free hydrogen and a catalyst composition comprising (a) a support material consisting essentially of alumina, (b) palladium metal and (c) nickel, under such reaction conditions as to convert at least a portion of neohexane to neopentane.

2. A process in accordance with claim 1, wherein said reaction conditions comprise a temperature of about 50° to 400° C., a hydrogen pressure to about 5 to about 1,000 psia, a molar ratio of free hydrogen to neohexane of about 0.5:1 to about 20:1, and a reaction time of about 1 second to about 10 hours.

3. A process in accordance with claim 2, wherein said temperature is about 100° to about 350° C., said hydrogen pressure is about 14 to about 200 psia, said molar ratio free hydrogen to neohexane is about 0.7:1 to about 5:1, and said reaction time is about 1 to about 60 minutes.

4. A process in accordance with claim 1 comprising the additional step of recovering formed neopentane.

5. A process in accordance with claim 1, wherein said catalyst composition comprises about 0.2 to about 20 weight-% palladium and about 2 to about 30 weight-% nickel.

6. A process in accordance with claim 1, wherein said catalyst composition comprises about 0.5 to about 10 weight-% palladium and about 4 to about 20 weight-% nickel, and has a surface area, determined by the BET method, of about 20 to about 700 m$^2$/g.

7. A process for preparing neopentane comprising the step of contacting a feed comprising neohexane with free hydrogen and a catalyst composition comprising (a) a support material consisting essentially of alumina, (b) palladium metal and (c) cobalt, under such reaction conditions as to convert at least a portion of neohexane to neopentane.

8. A process in accordance with claim 7, wherein said catalyst composition comprises about 0.2 to about 20 weight-% palladium and about 2 to about 30 weight-% cobalt.

9. A process in accordance with claim 7, wherein said catalyst composition comprises about 0.5 to about 10 weight-% palladium and about 4 to about 20 weight-% cobalt, and has a surface area, determined by the BET method, of about 20 to about 700 m$^2$/g.

10. A process in accordance with claim 7, wherein said reaction conditions comprise a temperature of about 50° to about 400° C., a hydrogen pressure of about 5 to about 1,000 psia, a molar ratio of free hydrogen to neohexane of about 0.5:1 to about 20:1, and a reaction time of about 1 second to about 10 hours.

11. A process in accordance with claim 10, wherein said temperature is about 100° to about 350° C., said hydrogen pressure is about 14 to about 200 psia, said molar ratio of free hydrogen to neohexane is about 0.7:1 to about 5:1, and said reaction time is about 1 to about 60 minutes.

12. A process in accordance with claim 7 comprising the additional step of recovering formed neopentane.

13. A process for preparing neopentane comprising the step of contacting a feed comprising neohexane with free hydrogen and a catalsyt composition comprising (a) a support material consisting essentially of alumina, (b) palladium, (c) nickel and (d) cobalt, under such conditions as to convert at least a portion of neohexane to neopentane.

14. A process in accordance with claim 13, wherein said catalyst composition comprises about 0.2 to about 20 weight-% palladium and from about 2 to about 30 weight-% of a nickel plus cobalt mixture.

15. A process in accordance with claim 14, wherein said catalyst composition comprises about 0.5 to about 10 weight-% palladium and has a surface area, determined by the BET method, of about 20 to about 700 m$^2$/g.

16. A process in accordance with claim 13, wherein said reaction conditions comprise a temperature of about 50 to about 400° C., a hdyrogen pressure of about 5 to about 1,000 psia, a molar ratio of free hydrogen to neohexane of about 0.5:1 to about 20:1, and a reaction time of about 1 second to about 10 hours.

17. A process in accordance with claim 16, wherein said temperature is about 100° to about 350° C ., said hydrogen pressure is about 14 to about 200 psia, said molar ratio of free hydrogen to neohexane is about 0.7:1 to about 5:1, and said reaction time is about 1 to about 60 minutes.

18. A process in accordance with claim 13 comprising the additional step of recovering formed neopentane.

* * * * *

UNITED STATES PATENT AND TRADEMARK OFFICE
CERTIFICATE OF CORRECTION

PATENT NO. : 4,940,829
DATED : July 10, 1990
INVENTOR(S) : Charles A. Drake

It is certified that error appears in the above-identified patent and that said Letters Patent is hereby corrected as shown below:

Claim 2, column 5, line 33, delete "to" after "pressure" and insert --- of --- therefor.

Claim 3, column 5, line 40, insert --- of --- between "ratio" and "free".

Signed and Sealed this

Seventeenth Day of September, 1991

Attest:

HARRY F. MANBECK, JR.

Attesting Officer

Commissioner of Patents and Trademarks